US005840318A

United States Patent [19]
Marshall et al.

[11] Patent Number: 5,840,318
[45] Date of Patent: Nov. 24, 1998

[54] METHODS AND COMPOSITIONS FOR MODULATING IMMUNE SYSTEMS OF ANIMALS

[75] Inventors: William E. Marshall, Bedford Hills; Michael K. Hoffmann, New York, both of N.Y.

[73] Assignee: Immunom Technologies, Inc., Bedford Hills, N.Y.

[21] Appl. No.: 739,264

[22] Filed: Oct. 29, 1996

Related U.S. Application Data

[63] Continuation-in-part of Ser. No. 517,016, Aug. 18, 1995, abandoned, which is a continuation-in-part of Ser. No. 376,175, Jan. 20, 1995, abandoned, which is a continuation-in-part of Ser. No. 59,745, May 11, 1993, abandoned.

[51] Int. Cl.⁶ .......................... A61K 25/66; A61K 39/02; A61K 35/74
[52] U.S. Cl. .................. 424/282.1; 424/93; 424/93.1; 424/92; 424/115; 424/278.1; 424/433; 424/434; 424/464
[58] Field of Search ............................... 424/93, 93.1, 92, 424/115, 433, 434, 464, 278.1, 282.1; 426/61; 514/2

[56] References Cited

U.S. PATENT DOCUMENTS

| | | |
|---|---|---|
| 3,320,130 | 5/1967 | Henry . |
| 3,953,609 | 4/1976 | Farr .......................................... 426/2 |
| 3,984,575 | 10/1976 | Farr ......................................... 426/61 |
| 4,314,995 | 2/1982 | Hata ........................................ 424/93 |
| 4,347,240 | 8/1982 | Mutai et al. ......................... 424/282.1 |
| 4,579,734 | 4/1986 | Hata et al. ........................... 424/93.45 |
| 4,849,506 | 7/1989 | Ransom et al. ......................... 530/351 |
| 4,975,467 | 12/1990 | Ku et al. ................................. 514/712 |
| 5,041,427 | 8/1991 | Takayama et al. ....................... 514/53 |
| 5,055,447 | 10/1991 | Palladino et al. ........................ 514/12 |
| 5,082,657 | 1/1992 | Ransom ................................. 424/85.1 |
| 5,082,838 | 1/1992 | Naka et al. ............................. 514/211 |
| 5,151,498 | 9/1992 | Buescher et al. ....................... 530/372 |
| 5,157,039 | 10/1992 | Nielsen et al. ......................... 514/311 |
| 5,158,939 | 10/1992 | Takayama et al. ...................... 514/53 |
| 5,413,785 | 5/1995 | Nanji ................................... 424/93.45 |
| 5,538,733 | 7/1996 | Emery ................................... 424/422 |

FOREIGN PATENT DOCUMENTS

| | | |
|---|---|---|
| 1298556 | 4/1992 | Canada . |
| 0 416 892 A1 | 3/1991 | European Pat. Off. . |

OTHER PUBLICATIONS

Brain, Ch. 14, *Handbook of Physiology—The Respiratory System I* (1985).
Kinoshita et al., *Int. J. Immunopharmac.* 14(2):205–211 (1992).
Raybourne, et al., *Infect. and Immun.* 62:665–672 (Feb. 1994).
Simpson et al., *Crit. Care Med.*, 19:1060–1066 (1991).
Perkins et al., *Am. J. Resp. Cell Biol.*, 4:532 (1991).
Kato et al., *Microbiol. Immunol*, 27(7):611–618 (1983).
Gold et al., *Infect. &Immun.* 49:731–741 (Sep. 1985).
Archer et al., *U.K. Biochem Soc. Trans.*, 19;404S (Jul. 1991).
Kantengwa et al., *Infect. & Immun.*, 61:1281–1287 (Apr. 1993).
Agace et al., *Infect. & Immun.* , 61:602–609 (Feb. 1993).
Popova et al *Inf. & Immunopharm* , 15(1):25–37 (1993).
Kineshita et al *Inf. & Immunopharm*, 14(2):205–211 (Feb. 1992).
Perdigon et al *J. of Food Protection*, 19(12):986–989 (Dec. 1986).
Perdigon et al *J. of Dairy Sci.*, 70(5):919–926 (1986).
Kuwabara et al . . . *Vet. Sci.*, 50(3):665–672 (1988).
Perdigon et al *Infect. and Immunity*, 53(2):404–410 (1986).
Kato et al., *Microbiol. Immunol.*, 27:611–618 (May 1983).
Mitsuoka, *J. Indus. Micro.*, 6:263–268 (1990).
DeSimone et al., *Immunopharm. & Immunotox.*, 14:331–340 (1992).
Perdigon et al.,*J. Food Protection*, 53:404–410 (May 1990).
Perdigon et al., *Immunology*, 63:17–23 (1988).
Perdigon et al., *J. Dairy Res.*, 57:255–264 (1990).
Guencheva et al *Inf & Immuno.* 14(8):1429–1436 (1992).
Lidbeck et al *Human Health: The Contribution of Microorganisms* et. Saw Gibson, Springer Valae, New York, Chap. 6, pp. 95–110 (1994).
Lidbeck et al *Scand. To Infect Dis.*, 19:531–537 (1987).
Lidbeck et al *J. of Concv. Prev.*, 1:341–353 (1992).
Lessard *Can J. Anim. Sci.*, 67509–516 (Jun. 1987).
Hack et al *Infect. & Immun.* 60:2835–2842 (Jul. 1992).
Perdigon et al., *J. Dairy Res.* 57:255–264 (1990).
DeSimone et al., *Dietetics in the 90's, Role of the Dietician/Nutritionist*, pp. 177–180 (1988).
Zeigler–Heitbrock, et al.,*Int. J. Cancer*, 41:456–461 (1988).
*Bergy's Manual of Systematic Bacteriology* 2, 2:1208–1234, Williams & Wilkins, Baltimore, MD (1986).
Schleifer, et al., *Bacter. Rev.* 36:407, Fig. 9 (1972).
Dibb et al, *Infect. & Immun.* 60:3052–3058 (Aug. 1992).
Steinshamn et al., *Infect. & Immun.,* 60:4003–4008 (Oct. 1992).
Tuomanen et al., *J. Infect. Dis.* 151:859–868 (May 1985).
Riesenfeld–Orn et al. *Infect. & Immun.*, 57:1890–1893 (Jul. 1989).
Bhakdi et al., *Infect. & Immun.*, 59:4614–4620 (Dec. 1991).
De Vuyst et al. 1996 Microbiology 142 p. 817–827, Jan. 1, 1996.

*Primary Examiner*—Marian C. Knode
*Assistant Examiner*—Mary K. Zeman
*Attorney, Agent, or Firm*—Zarley, McKee, Thomte, Voorhees & Sea

[57] ABSTRACT

Methods and compositions for modulating the immune system of animals by activating macrophages to release cytokines and down-regulating their sensitivity to bacterial endotoxin and to conversion to cytotoxic phenotypes by the administration of stress response factors released by stressed bacteria.

Methods and compositions for protecting the viability of liquid or dried cultures of bacteria by the administration of stress response factors released by stressed bacteria.

14 Claims, 3 Drawing Sheets

METHODS AND COMPOSITIONS FOR MODULATING IMMUNE SYSTEMS OF ANIMALS

CROSS REFERENCE TO RELATED APPLICATION

This application is a continuation-in-part of U.S. patent application Ser. No. 08/517,016 filed on Aug. 18, 1995, now abandoned, which is a continuation-in-part of U.S. patent application Ser. No. 08/376,175 filed on Jan. 20, 1995, now abandoned, which is a continuation-in-part of U.S. patent application Ser. No. 08/059,745 filed on May 11, 1993 now abandoned.

FIELD OF THE INVENTION

This invention relates to methods and compositions for modulating immune responses of animals or humans. More particularly, the invention relates to methods of modulating immune responses of animals or humans by administering effective amounts of compositions harvested from stressed bacteria which include stress response factors (SRFs) that act to activate and modulate circulating macrophages.

BACKGROUND OF THE INVENTION

We have found that stressed bacteria release polymers of nucleic acids, proteins and peptidoglycans and their partial and complete hydrolysates. Although this response is associated with the deaths of 75–90% of the population, these released products preserve the viability of the survivors. Thus, the addition of these products to stored bacterial preparations will have commercial importance in maintaining their viability.

In addition, we have found that these released products stimulate the immune system. This is important when they are released by bacteria populating the external surfaces of an animal or human, e.g., the mouth, nose, outer ear, oropharyngeal cavity and vagina. The stressors that induce their release are common to commensal bacteria, e.g. over-crowding, nutrient deprivation and exposure to antibiotics. We have found that the oligomeric fraction having a molecular weight <10 kDa and, in particular, between 500. and 3,000. are readily absorbed, are non-toxic, and both active and modulate the immune system. Macrophages are activated to release cytokines at levels deemed helpful to combating infections and down-modulated to prevent their over-activation with the subsequent release of host-threatening levels of cytokines and becoming overly cytotoxic resulting in perforation of vessels.

We believe that through co-evolution with bacteria, the macrophage has adapted a pre-emptory reaction to the presence of the oligomers that prepares the immune system to defend the host against infection. For example, when commensal bacteria are over-crowded by the presence of growing pathogens, they will release readily absorbable, non-toxic oligomers which activate tissue macrophages to release Interleukin-1, IL-1, Interleukin-6, IL-6 and Tumor Necrosis Factor, alpha, TNFα which stimulate other cells of the immune system. After being so activated, exposed macrophages down-regulate the surface receptors, CD-14 and CD-16, thereby desensitizing the cell from over-activation by the subsequent interaction with bacterial toxins if infection occurs.

Likewise, bacteria attempting to invade horizontally onto sterile tissue, (e.g. from the outer to the inner ear, from the nose to the sinus, from vagina to uterus), encountering nutrient deprivation will release these oligomers which will serve to alert the host to a potential penetration onto a sterile area or into sterile tissue.

As sentry cells, macrophages circulate in the blood and lymph as well as reside in specialized endothelial cells, tissues and organs. They are among the host's first line of defense, releasing interleukin signals and destroying microbes and diseased cells of the host. Twenty different interleukins can be released by receiving cells, modifying, amplifying, restricting and dampening messages as the system is stimulated. Thus, the macrophage's signal is key to initiating and enforcing the appropriate immune response. In an infection, bacterial endotoxin (lipopolysaccharide LPS), binds to the CD-14 surface receptor on the macrophage, up-regulating it and inducing the release of yet higher levels of IL-1, IL-6 and TNF. These signals, in turn, induce fever, fatigue, cardiovascular hypotension, renal failure and death in "septic shock".

To fulfill their role as destroyers of diseased cells of the host, CD-16 recognizes the Fc portion of antibodies. Diseased cells of the host induce the formation of antibodies against presented antigens on their surfaces. The Fc portion of the antibody is received by the CD-16 receptor on the macrophage. Through a complex of reactions, the attached cell is destroyed. By down-regulating the numbers of CD-16 receptors on the surface of the macrophage, the oligomers released by stressed bacteria help to ensure that the macrophage does not become over-activated by IL-10, thereby destroying healthy host cells. This is the case in septic-shock and AIDS, where high numbers of overly active cytotoxic macrophages destroy healthy T-cells.

Thirteen different species of animal-associated bacteria were found to release products when stressed. However, the distribution of polymer:oligomer:monomer was not equal among the species tested. The polymeric fraction (>10 kDa) was toxic when injected into mice, producing a ruffled fur coat, huddling and diarrhea. In vitro assays using human peripheral blood macrophages indicated that the monomeric fraction, (0.5 kDa) did not induce the release of significant levels of interleukins. However, the oligomeric fraction, (between 0.5 and 10. kDa) activated and modulated macrophages, was non-toxic when injected into mice and protected them against a subsequent lethal challenge of injected endotoxin. Therefore, not all strains of bacteria, even of the same specie, release levels of oligomers sufficient to protect animals against a subsequent bacterial invasion.

We believe that the oligomeric stress-response-factors, (SRFs), (between 0.5 and 10. kDa) are a rich new source of natural, normally-occurring immune modulators that can be safely used to protect animals and humans from infections and over-stimulation of their immune system. In addition, this fraction contains compounds that could be used to adjust the expression of individual surface receptors on macrophages to recenter a dysfunctional immune system. Furthermore, in vitro testing indicates their potential role as adjuvants by stimulating the release of IL-12.

An additional discovery is the finding that feral colonies of bacteria yield more oligomeric SRFs when initially stressed than non-feral or laboratory strains. However, inducing a stress upon the repropagated surviving colonies of a stressed laboratory strain will yield a level of oligomeric SRFs comparable to that occurring when the feral strain was stressed. Since macrophages are not activated by the monomeric SRFs, released oligomeric SRFs may reflect a state of virulence.

The discovery of the release of immune-activating and modulating factors has broad implications to improving the immune response through diets and pharmaceutical preparations for humans and animals. Fermented products e.g. milk, cheese, yogurts) contain viable bacteria, which, when transferred to the nutrient deprived environment of the mouth release SRFs. If such products were formulated to extend the dwell-time in the mouth, more SRFs would be released activating and modulating a greater local immune response.

Livestock are routinely fed silage, a fermented product containing high levels of viable harmless bacteria. When ingested and chewed as cud, the silage bacteria release immune-activating SRFs. The proper selection of harmless bacteria that ferment silage and grains and also release significant levels of SRFs will help improve the health of livestock.

Direct-fed microbials and probiotics are harmless bacteria which are grown in a rich media, concentrated, dried and fed to animals either as a powder for top-dressing or in gel forms for oral inoculation. These products provide a health benefit to the animal in combating infections relating to the shipping and weaning. Analysis of commercial products indicates the presence of oligomeric SRFs as well as the release of oligomeric SRFs when transferred to saliva or to a nutrient-reduced environment. We believe the presence and release of SRFs explains their effectiveness. This discovery permits the administration of a sterile, stable, probiotic of known dose for livestock and poultry. Currently, viability of probiotics is believed necessary for effectiveness. A sterile, stable product will allow distribution without refrigeration and provide a known dose.

An object of this invention regarding human health is to provide an oral pharmaceutical to help prevent infections.

A further object of this invention is to provide topical pharmaceutical preparations for the activation and modulation of local immune systems to protect against ear, nose and vaginal infections.

Another object of this invention is to use parenteral injections of individual components of these pharmaceutical preparations to treat septic shock.

An additional object of this invention is to use individual components of these pharmaceutical preparations as adjuvants in conjunction with vaccination.

And a further object of this invention is to provide pharmaceutical compositions to down regulate the cytotoxicity of macrophages and prevent their destruction of normal T-cells in persons suffering from HIV infections.

And finally, an object of this invention is to use SRFs as protectants in the storage of starter and other bacterial cultures of use in the food industry.

Numerous patents teach the healthful benefits of administering specific viable bacteria to humans and animals either orally or parenterally to provide local immune stimulation. Additionally, the prior art recognizes the importance of modulating interleukin release but does not teach the use of safe, natural, normally-occurring products which are effective when taken orally. However, this discovery teaches the administration of sterile, stable, controlled doses of the active principle, oligomeric SRFs, rather than unstable, viable microorganisms. U.S. Pat. No. 4,975,467 teaches methods by which synthetic compounds can be used to inhibit the release of IL-1 thereby alleviating the induction of its pathophysiologic conditions. U.S. Pat. No. 5,055,447 provides methods and compositions for the prevention of septic shock by administering growth factor-$\beta$. This patent teaches the use of administering a signal compound to intercept or modify existing signals. U.S. Pat. No. 5,041,427 and 5,158,939 teach the use of a non-toxic LPS from R. spaeroides, ATCC 17023 to desensitize macrophages to toxic LPS. Since R. spaeroides has an unusual lipid A structure, it may not be effective as a desensitizing agent. U.S. Pat. No. 5,157,039 supports the clinical importance for controlling IL-1 release by macrophages by teaching the use of two non-natural quinolinol compounds which appear to be non-selective in IL inhibition.

And lastly, bacteria release these products to protect the surviving 10 to 25% of their culture from death. During the aforementioned stress, 70 to 90% of the bacterial population lose viability. The viability of the survivors is maintained by the presence of SRFs. A further application of this invention is therefore, the use of SRFs to improve the viable shelf-life of dried, frozen or liquid cultures of commercial importance, e.g. starter cultures for the dairy industry.

BRIEF DESCRIPTION OF THE FIGURES

FIG. 1 illustrates the distribution of <10 kDa SRFs released by a non-feral ATCC strain of L. caseii showing a relatively greater amount of non-activating monomers than activating oligomers. However, a higher proportion of oligomeric SRFs are released by the survivors of the initial stress which have been repropagated to $10^9$ CFU/ml and stressed in the same manner, FIG. 2.

FIG. 3 illustrates the <10 kDa SRFs released by the feral and virulent pathogen, L. monocytogenes.

SUMMARY OF THE INVENTION

Figure 1:
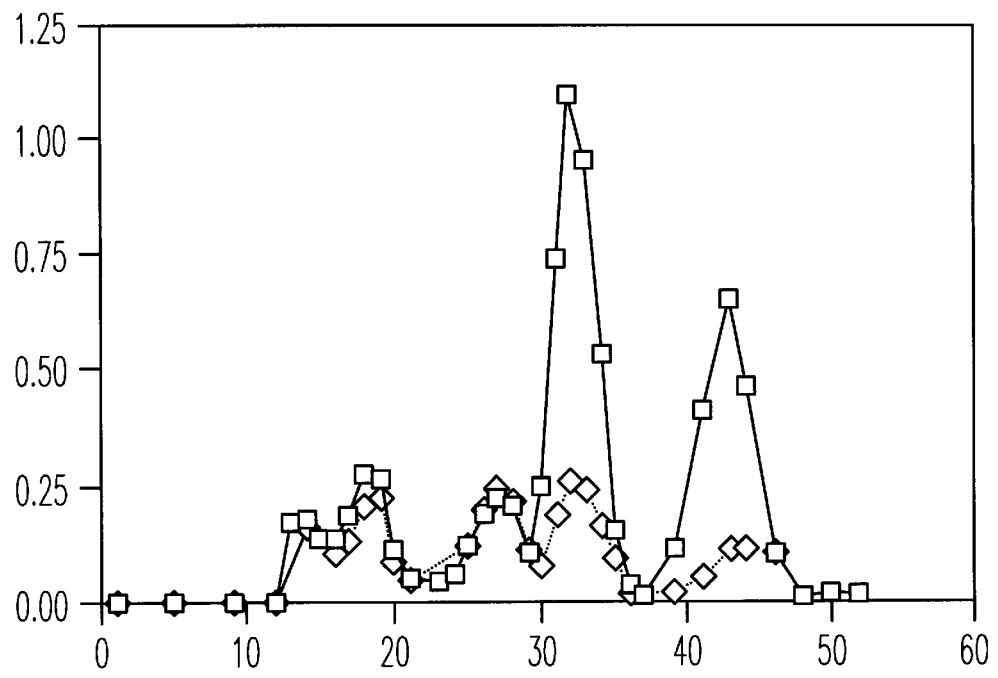
FIGS. 1, 2, and 3 depict the range of profiles of <10 kDa SRFs released by bacteria when cultures are transferred to an environment with fewer nutrients. The oligomeric fraction that activates and modulates macrophages is that eluted between 10 and 30 ml.
Figure 2:
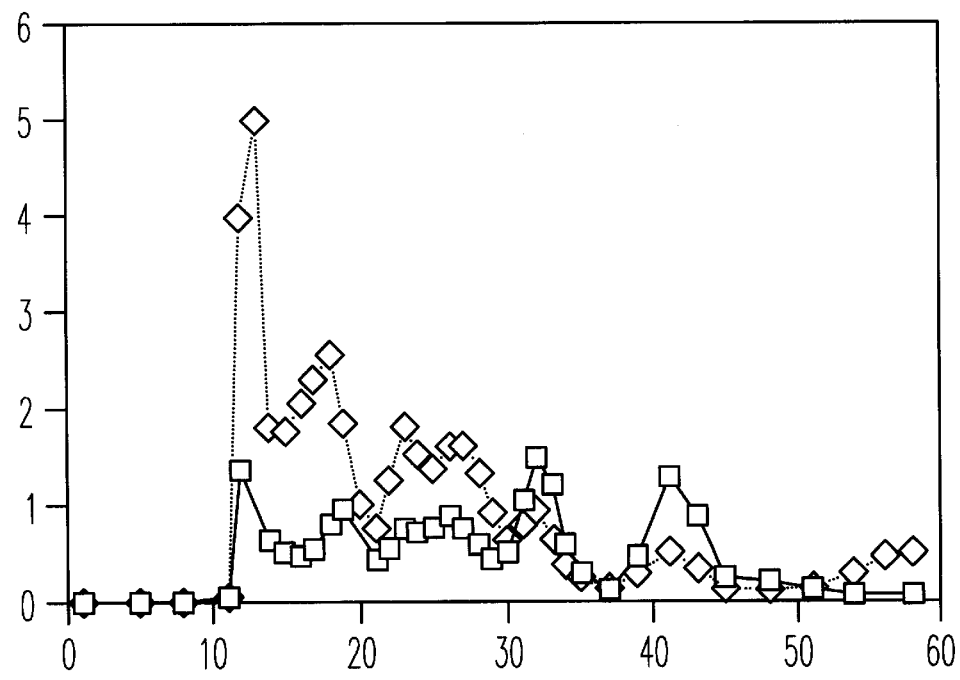
Figure 3:
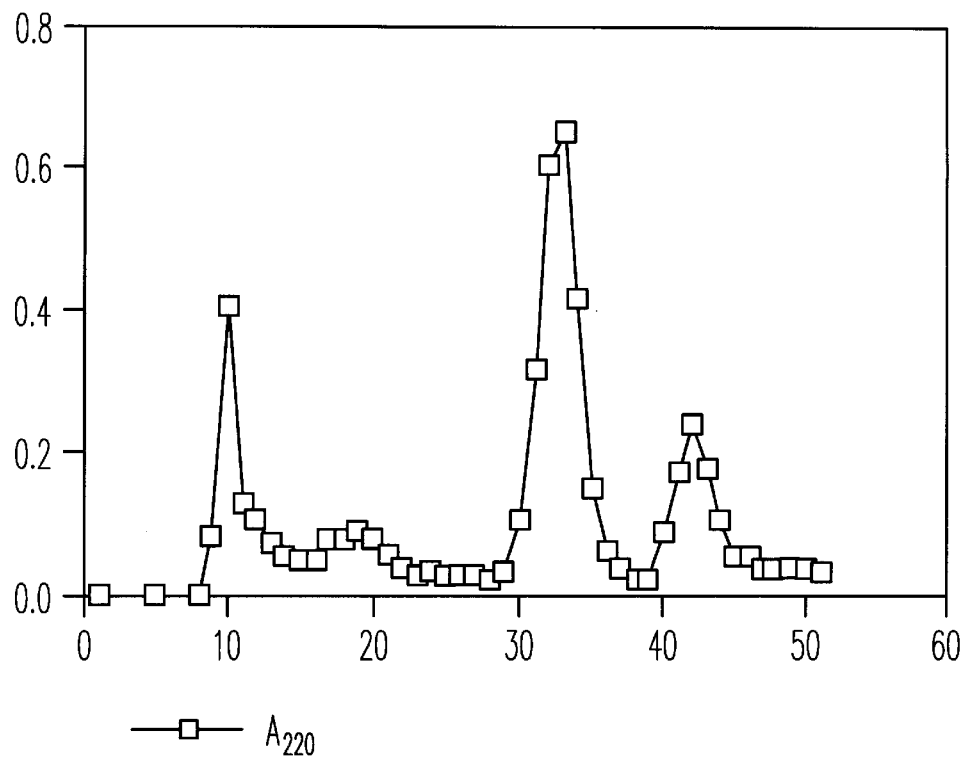
Figure 4:
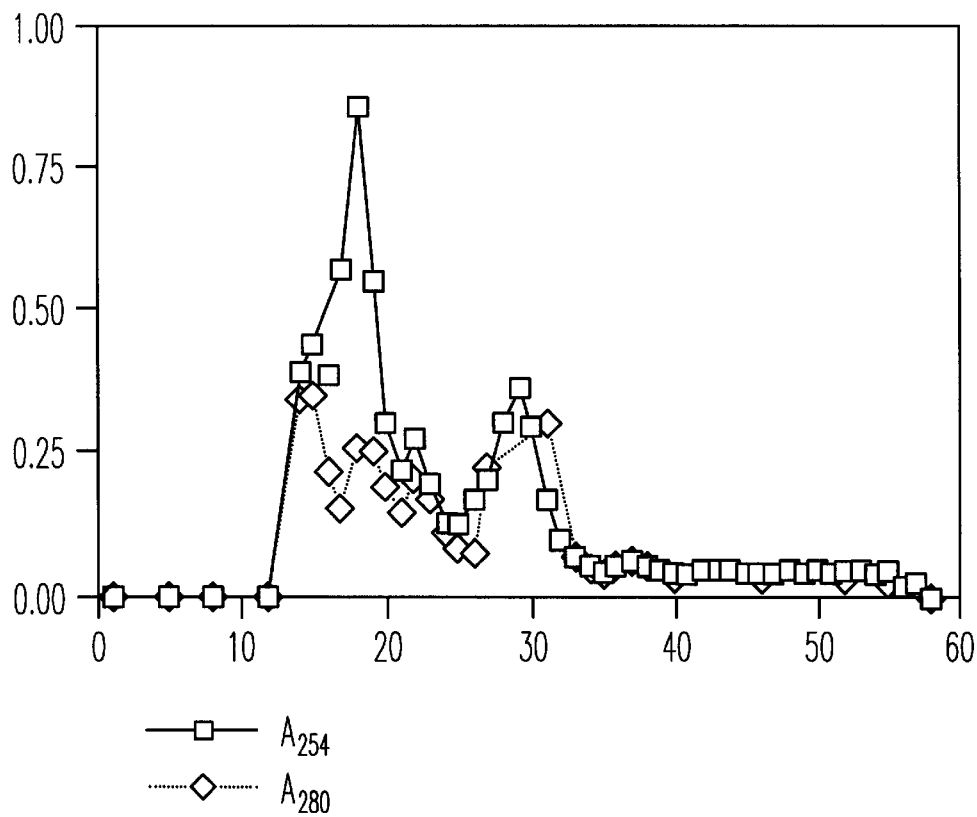
FIG. 4 shows the <10 kDa SRFs released by a direct-fed-microbial or animal probiotic commercially marketed which indicates the presence of macrophage-activating oligomers.
Figure 5:
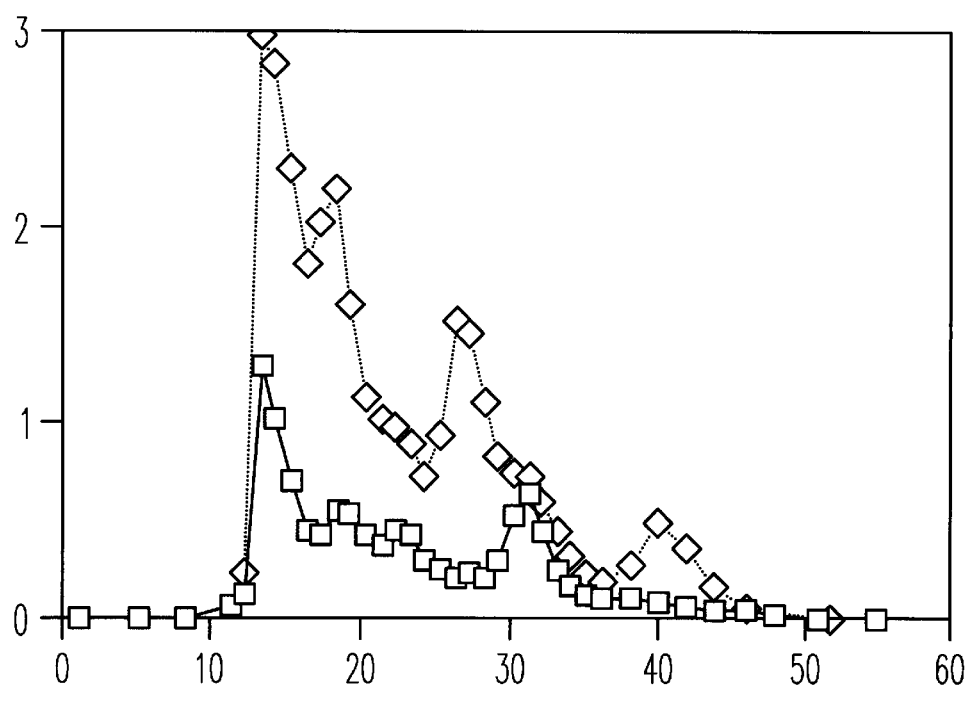
FIG. 5 shows the profile of <10 kDa SRFs released by whole corn silage when transferred to saliva or 0.01M phosphate buffer, pH 7.5 in buffer at pH 4., only 25% of the level of SRFs were released indicating that the SRFs resulted from bacterial action rather than from leaching of the plant components.

This invention comprises pharmaceutical compositions and methods of use of the same for activating and modulating immune responses in animals. The phrase "modulating an immune response in animals" as used herein includes (a) stimulating an immune response by activating macrophages to release immune stimulating interleukins IL-1, IL-6 and TNF (for example to prevent or combat infections); (b) down-regulating the CD-14 receptor of macrophages to prevent over-stimulation by endotoxin leading to the over-production of IL-1, IL-6 and TNF, associated with systemic inflammation, cardiovascular dysfunction, shock and death; (c) down-regulating the CD-16 receptor of macrophages to prevent over-stimulation by IL-10 leading to the over-conversion of macrophages to their cytotoxic phenotype with its potential for excessive destruction of host cells, e.g. endothelial cells lining blood vessels and T-cells.

DETAILED DESCRIPTION OF THE INVENTION

Under normal and naturally-occurring stresses, bacteria have been found to release products named stress response factors, (SRFs). The products less than 10 kDa in size are non-toxic and contain further a group of compounds of oligomeric size, i.e. 0.5 to 10 kDa that activate and modulate macrophages.

The composition of the invention may be administered orally or parentally or topically to stimulate the immune system by: (1) activating macrophages to release cytokines, in particular IL-1, IL-6 and TNF required to initiate an immune response to prevent or reduce infection and, (2) by counteracting the potential pathologic role of macrophages in over-stimulating the inflammatory response locally (for example rheumatoid arthritis and other auto-immune diseases) or systemically (for example septic shock.) At high levels of the administered compositions, highly expressing macrophages are induced to cell-suicide or apoptosis, thereby ensuring protection against immune dysfunction.

The methods of obtaining the composition of the invention comprise growing a selected bacteria in a media outside of the animal to a selected level of enumeration, stressing the selected bacteria thereby initiating the release of stress response factors and thereafter, collecting the supernatant containing the stress response factors. Preferably the stressing of the selected bacteria to induce the release of stress response factors is accomplished by reducing the availability of nutrients to the bacteria. Most preferably this is accomplished by one or more of the following methods after propagating bacteria to the selected level of enumeration. (1) removing the bacteria from the media by centrifugation and suspending the bacteria in a non-nutritive buffer; (2) adding effective antibiotics to preparations of sensitive bacteria; (3) adding additional bacteria to the media; (4) reducing the volume of the media; (5) removing nutrients from the media; and (6) altering the pH of the media to affect the bioavailability of nutrients from the media.

Most preferably the method of stressing the bacteria is by removing the bacteria from their media while in mid-log growth (about $10^9$ CFUs per ml) and resuspending them at a 5-fold concentration in a non-nutritive phosphate buffer at pH 7.5 for 12 hours at 37° C. The appearance of these factors can be followed by monitoring absorbencies in the ultraviolet, at 220 and preferably at 254 nm. It was discovered that supernatants containing SRFs with a molecular weight greater than 10 kDa were toxic when administered parenterally to mice, so in a preferred embodiment the invention comprises removing all substances greater than 10 kDa by means such as filtration. Thus the supernatant may be filtered so that all SRFs greater than 10 kDa are removed and those of a size less than 10 kDa are retained in solution. Serial stresses may be induced on the survivors to obtain additional SRFs.

The amount of total SRFs released depends on: (a) the level of bacteria; an optimum level is $5 \times 10^9$ to $3 \times 10^{10}$ CFUs per ml; at higher levels, fewer SRFs are released per cell; (b) the severity of stress; transferring bacteria from their log phase in rich media into a non-nutritive buffer will produce several fold more SRFs than transferring bacteria from their stationery phase in a rich media into a minimal media; (c) strains selected from the wild provide more SRFs than laboratory strains; however, stressing laboratory strains, re-propagating and stressing the survivors yields significant levels of oligomeric SRFs, (d) the pH of the release solution; pH values below 4.8 induce the release of approximately one-fourth the level of those released at pH 7.5; (e) the temperature; release can be observed at 40° C., an optimum is reached at approximately 40° C.; (f) the time; release begins immediately and plateaus at about 9 to 12 hours unless the supernatant is continually being drawn-off; (g) the molarity and ionic strengths of the releasing solution appear to be of minor significance in the release of SRFs.

Generally, for accumulation of the composition of the invention, after incubation, the SRF-containing supernatant is rendered bacteria-free by filtering through a 0.22 μm filter to yield a sterile preparation containing all sizes of SRFs. Typically, the total SRF fraction consists of 5–20% polymers larger than 30 kDa, 0.2–20% oligomers between 0.5 and 10 kDa and 0.5–95% monomers less than 0.5 kDa in size. Each of these fractions consist of nucleic acids, peptidoglycans and peptides in varying molecular sizes. The oligomeric fraction between 0.5 and 10 kDa is non-toxic, readily absorbable and activates macrophages. Daily injections of a protective dose of <10 kDa SRFs for five consecutive days did not cause apparent toxicity, i.e. cessation of eating, ruffled fur, huddling, or diarrhea.

Since the ultraviolet spectrum of SRFs indicates a maximum of 254 nm, one Arbitrary Unit (AU) of SRFs was established as that level of SRFs providing an optical density of 0.001 through 1 cm. of a solution.

SRFs from 15 strains of animal-associated, Gram-positive and Gram-negative, aerobic and anaerobic bacteria representing both harmless and virulent pathogens release SRFs as evidenced by the rise in A254 during stress induced by nutrient reduction. However, the distribution of sizes within 10 to 0.5 kDa was not equal across all strains.

This invention teaches the selection of organisms and the conditions employed to stress them to yield a maximum level of oligomeric SRFs, preferably between 0.5 and 3 kDa.

This invention teaches the improvement of two natural conditions: the consumption of food by humans or feedstuffs by livestock which are rich in microbial populations. Pasteurized fresh milk contains about $10^4$ CFU of bacteria per ml. Fermented dairy products (milk, yogurts, cheeses) typically contain $10^{6-8}$ CFUs per ml. of populations of harmless bacteria in stationery phase. When transferred by eating into a nutrient poor environment, the mouth, SRFs are released at corresponding levels. If the dwell-time in the mouth can be increased by gelling or thickening agents being applied to the food, the release of SRFs and delivery to oropharyngeal macrophages can be increased to immune-stimulating levels. This, we believe explains the frequently reported observations regarding immune stimulation and the benefits derived from consuming fermented foods. Fresh vegetables containing high levels of harmless bacteria will also stimulate local oral macrophages by releasing SRFs during eating.

Similarly, the practice of administering preparations of $10^{8-10}$ CFUs of harmless viable bacteria to livestock to reduce the incidence of infections during shipping and weaning results in the release of SRFs by bacteria lyophilized from rich media. Superior products can be formulated by selecting bacteria that release a predominance of oligomeric SRFs, 0.5 to 3 kDa in sterile formulations that prolong dwell-time in the mouth. In addition, these preparations can contain added SRFs to maintain their viability during storage. Furthermore, probiotic preparations can be delivered bacteria-free by separating and packaging the active fraction, SRFs.

Additionally, bacterial inoculants of $10^{8-10}$ CFUs of bacteria are commonly added to stored grains and crops to assist and speed the fermentation of plant materials into readily available nutrients for livestock. Presently, strains are selected for their ability to propagate rapidly on the targeted grains and crops. The "probiotic" effect of enhancing the animal's resistance to infection which is often observed from consuming inoculated grains and silages is due to the stimulation of macrophages by SRFs released when these bacteria are introduced into the nutrient-poor environment of the animal's mouth. The probiotic effectiveness of crop inoculants can be increased by selecting strains specific to certain crops plus having the capability to release significant levels of readily-absorbable, non-toxic oligomeric SRFs as taught herein.

The generation of SRFs is not to be confused with the generation of shock proteins resulting from changes in temperature or other conditions. Shock proteins have a molecular weight greater than 10 kDa (typically 30–150 kDa) and their release is not associated with loss of viability. They represent increased synthesis of certain proteins plus the de novo synthesis of new proteins.

The following examples are offered to illustrate but not limit the invention.

EXAMPLES

1

By measuring the release of A254-absorbing compounds, we observed the release of SRFs from approximately $2 \times 10^{10}$ CFU after 10 hours of incubation at 37 C in 0.01M phosphate buffer, pH 7.5. The average number of Arbitrary Units (AU) per ml ±50% from three experiments according to Example 2 were:

|                  |              |
| ---------------- | ------------ |
| L. acidophilus   | 3000.AU/ml   |
| L. caseii        | 7000.        |
| L. fermentum     | 3500.        |
| L. plantarum     | 4000.        |
| L. monocytogenes | 24000.       |
| S. aureus        | 10000.       |
| S. typhimurium   | 9000.        |
| P. acidolactici  | 6500.        |
| B. coryneforme   | 6200.        |
| E. coli          | 4400.        |
| E. faecium       | 7000.        |
| S. pyogenes      | 12000.       |
| K. pneumoniae    | 8500.        |

Colonies of *S. aureus* obtained from a patient, were transferred from agar to 2 ml of Tryptone-Soy-Broth (TSB) and held at 37° C. until turbid, about 4 hours. Thereafter, the volume of TSB was doubled every hour until the absorbancy at 540 nm reached 1.5, corresponding to about $2 \times 10^9$ Colony-Forming-Units/ml. (CFU's) in a volume of 60 ml. The pellet of bacteria was centrifuged at 8000×g for 10 minutes and washed by resuspending in a half-volume of cold saline and centrifuging. The pellet was then suspended in 6 ml of 0.05M phosphate buffer at pH 7.5 containing 0.9% NaCl and incubated at 37° C. for 16 hours. The measured Absorbance at 254 nm ($A_{254}$) immediately began to rise exponentially, reaching a plateau of 12000 after 12 hours.

The supernatant was collected by centrifugation and sterilized by passing through a 0.22 µm filter. The <10 kDa SRFs were obtained by passing the sterile supernatant through a filter with a molecular weight cutoff of 10,000. Typically, the $A_{254}$ of the <10 kDa fraction was 75 to 90% of the total supernatant.

3

*L. monocytogenes* was propagated in Brain-Heart-Infusion (BHI) as described in Example 1 to yield a <10 kDa fraction of SRFs with an $A_{254}$=22. or 22000 Arbitrary Units (AU)/ml.

4

*E. coli* was propagated in Minimal-Media-Davis (MMD) as described in Example 1 to yield a <10 kDa fraction of SRFs with an $A_{254}$=8.000 or 8000 AU/ml.

5

*L. caseii* was propagated in Mann-Rogosa-Sharpe broth, (MRS) as described in Example 1 to yield a <10 kDa fraction of SRFs with an $A_{254}$=9.250 or 9250 AU/ml after the initial incubation. A second and third serial incubation of 16 hours each to release SRFs yielded 12000 AU/ml and 3250 AU/ml, respectively.

6

The <10 kDa SRFs from *L. caseii* were prepared according to Example 5 and were tested for their ability to activate macrophages to release interleukins and down-regulate CD-14 and CD-16 surface receptors by selective deletion of macrophages.

Heparinized peripheral blood was collected from human volunteers and the leukocytes isolated by centrifuging in Ficoll. The buffy coat containing the leukocytes was collected and distributed into wells of a micro-titer plate at a concentration of $10^5$ per well. The macrophages were separated by adherence to the plastic walls of the plate during 4 hours of incubation of 37° C. in a $CO_2$-rich atmosphere. RPMI 1640 culture media was added providing a final concentration of macrophages of 1 to $3 \times 10^6$/ml. Solutions of phosphate-buffered-saline at pH=7.5 (PBS), or 0.1M phosphate, pH=7.5 containing SRFs were added in volumes equal to one-tenth the volume of RPMI and incubated as mentioned.

During incubation, aliquots were removed and viable macrophages were counted visually in a hemacytometer. The interleukins IL-1α, IL-6 and TNFα were determined using commercial cytokine kits (R & D Systems, Minneapolis, Minn.). The levels of the surface receptors on the macrophages were determined by adding fluorescent monoclonal antibodies specific for CD-14 and CD-16 and measuring fluorescence in a FACScan flow cytometer. Data were analyzed by the Lysis-1 program.

|                          | Interleukins (pg/ml) |        |       | Surface Receptors* |       |
| ------------------------ | -------------------- | ------ | ----- | ------------------ | ----- |
| <10 kDa SRFs             | IL-1α                | IL-6α  | TNFα  | CD-14              | CD-16 |
| Control:                 | 0                    | 0      | 0     | 70                 | 70    |
| Total:                   |                      |        |       |                    |       |
| 800 AU/ml                | 25                   | 35000  | 2250  | 60                 | 60    |
| 80                       | 15                   | 22000  | 1700  | 70                 | 70    |
| 8                        | 8                    | 5000   | 8500  | 70                 | 70    |
| Oligomeric Fraction G-10:|                      |        |       |                    |       |
| 800                      | 550                  | 30000  | 2000  | 30                 | 30    |
| 80                       | 315                  | 21000  | 1600  | 50                 | 50    |
| 8                        | 80                   | 5000   | 900   | 60                 | 60    |

*Percentage of macrophages with highly expressed CD-14 and CD 16.

The levels of the surface receptor on the macrophages were determined by fluorescent antibody techniques in a flow cytometer. A bimodal distribution of fluorescence indicating high and low-expressing macrophages was observed.

The deletion of macrophages were determined by visual counting as taught in Example 3.

| G-10: Oligomeric SRFs | Deletion of Macrophages |
|---|---|
| 1000 AU/ml | 55% |
| 100 | 15 |
| 10 | 0 |
| none | 0 |

7

The <10 kDa SRFs from *L. monocytogenes* were prepared according to Example 3 and were injected into mice to protect them against a lethal dose of septic-shock inducing endotoxin.

Five week old female Balb/C mice were injected i.p. with 0.2 ml of the PBS solution containing 4800 AU of <10 kDa SRFs 18 hours before receiving an injection of 400 μg of LPS from *E. coli* O 188:B7, (Sigma, St. Louis, Mo.). The mice showed no adverse effects from the SRFs but became sick as evidenced by their cessation of feeding, ruffled fur and huddling together after the injection of LPS. After 32 to 48 hours they recovered fully. The mice that did not receive a pretreatment of SRFs died within 48 hours after the LPS injection.

| SRFs Injected Once Intraperitoneally | Percentage of Survivors After Receiving 400 μg LPS, i.p. |
|---|---|
| 4800 AU | 100% (2/2) |
| 1200 | 85 (6/7) |
| 300 | 8 (1/12) |
| none | 0 (0/10) |

8

The <10 kDa SRFs from *L. monocytogenes* were prepared according to Example 3 and fed to mice to protect them against a lethal dose of septic shock inducing endotoxin, LPS.

Five week old female Balb/C mice consumed 6000 AU of <10 kDa SRFs daily in 4 ml in their drinking water for 3 days before receiving an injection of 400 μg of LPS from *E. coli* O 188:B7. The mice showed no adverse effects from consuming the SRFs but became sick as evidenced by their cessation of feeding, ruffled fur and huddling together after the injection of LPS. After 32 to 48 hours they recovered fully. The mice that did not consume a pretreatment of SRFs died within 48 hours after the LPS injection.

| SRFs Consumed Daily in Drinking Water | Percentage of Survivors After Receiving 400 μg LPS, i.p. |
|---|---|
| 6000 AU | 100% (4/4) |
| 1000 | 75 (3/4) |
| none | 0 (0/10) |

9

To demonstrate the ability of SRFs to protect the viability of bacteria, 90000. AU of lyophilized <10 kDa SRFs collected from the total SRFs released by 10 ml of a culture containing *S. aureus* at $1 \times 10^{10}$ CFU per ml were added to a closed flask containing 100 ml of *M. elsdenii*, ATCC 25940, at $3 \times 10^9$ CFU per ml. *M. elsdenii*, an obligate anaerobe was left in its spent media at 25° C. The addition of SRFs protected the viability of 90% of the *M. eldsdenii* against oxygen and the toxic effects of its metabolic products.

| Time | Control | Control + 90000. AU of SRFs |
|---|---|---|
| Day 0 | $2.55 \times 10^9$ | $2.55 \times 10^9$ |
| Day 2 | $1.25 \times 10^9$ | $3.9 \times 10^9$ |
| Day 6 | $1.75 \times 10^8$ | $1.35 \times 10^9$ |

10

To demonstrate the stress-inducing effects of antibiotics, penicillin and streptomycin were added at a final concentration of 1% to a culture of *E. coli* ATCC 11775 growing to mid-log phase of $2.4 \times 10^8$ CFU/ml in shaking Davis Minimal Medium +0.1% dextrose. After 3 hours, aliquots were removed for enumeration and analysis for the generation of SRF.

| Time | Without Antibiotic | Antibiotic Added |
|---|---|---|
| 3 hours | $6 \times 10^8$ CFU/ml | $<1 \times 10^7$ CFU/ml |
| AU@254 nm | 390. | 630. |

To demonstrate the inducing effects of antibiotics on bacteria in stationery phase, propagating aliquots from the above experiment were allowed to pass into their stationery phase by continuing incubation for another 24 hours. Chromatography on Sephadex G-10 showed a profile similar to those of FIG. 1.

| Time | Without Antibiotic | Antibiotic Added |
|---|---|---|
| 3 hours | $6 \times 10^8$ CFU/ml | $4 \times 10^8$ CFU/ml |
| AU@254 nm | 470. | 690. |

As can be seen from the above examples, the invention accomplishes its stated objectives. Of course certain various from what has been illustrated and described can be made without departing from the spirit and scope of the invention and those are intended to be encompassed either literally or by the doctrine of equivalents.

What is claimed is:

1. A method for activating and modulating the immune system of an animal comprising:

(a) growing bacteria in a medium, wherein the bacteria is of a class selected from the group consisting of Lactobacillus, Staphylococcus, Streptococcus, Pseudomonas, Bacillus, Escherichia, Enterococcus, and Klebsiella;

(b) exposing said bacteria to biological, chemical or physical stress so that the bacteria release a stress release product into the medium;

(c) removing said bacteria from said medium and said stress release product to form a separated product;

(d) filtering said separated product through a filter having a 10,000 dalton molecular weight cutoff to obtain said stress release product; and (e) administering an effective amount of said stress release product to said animal.

2. The method of claim 1 wherein the step of stressing said bacteria is selected from the group consisting of:

altering the pH of said media to affect the bioavailability of nutrients in said media, removing nutrients from said media, crowding by reducing the volume of said media, adding additional bacterial to said media, and removing said bacteria from said media by centrifugation and resuspending said bacteria in a non-nutritive isotonic solution.

3. The method of claim 1 wherein said non-nutritive isotonic solution comprises 0.9% sodium chloride.

4. The method of claim 2 wherein said non-nutritive isotonic solution is 0.1M phosphate buffer having a pH of 7.5.

5. A method for modulating the immune system of an animal comprising:

administering to said animal an effective amount of a product released by bacteria in response to stress wherein the stress release product is made by a method comprising:
- (a) growing bacteria in a medium, wherein the bacteria is of a class selected from the group consisting of Lactobacillus, Staphylococcus, Streptococcus, Pseudomonas, Bacillus, Escherichia, Enterococcus, and Klebsiella;
- (b) exposing said bacteria to biological, chemical or physical stress so that the bacteria release a stress release product into the medium;
- (c) removing said bacteria from said medium and said stress release product to form a separated product;
- (d) filtering said separated product through a filter having a 10,000 dalton molecular weight cutoff to obtain said stress release product; and
- (e) administering an effective amount of said stress release product to said animal and further providing that the stress release product is administered to the animal in a delivery form selected from the group consisting of forms for parenteral delivery, gels for oral delivery, lozenges for oral delivery, nasal sprays, ear drops, vaginal creams, vaginal suppositories, and topical ointments.

6. The method of claim 5 wherein said animal is selected from the group consisting of humans, poultry and livestock.

7. The method of claim 5 wherein said stress release product is administered in a concentration of about 1000 to 50,000 AU of said stress release product/ml.

8. The method of claim 7 wherein said stress release product is administered orally or parenterally.

9. The method of claim 5 wherein the stress release product has a size of between 0.5 and 3 kDa.

10. The method of claim 5 wherein said stress release product is administered daily for five consecutive days.

11. The method of claim 5 wherein said stress release product is administered with a killed pathogen.

12. A method of maintaining the viability of bacteria during storage and shipment comprising:

administering to said bacteria a product released by bacteria in response to stress, wherein the stress release product is made by a method comprising:
- (a) growing bacteria in a medium, wherein the bacteria is of a class selected from the group consisting of Lactobacillus, Staphylococcus, Streptococcus, Pseudomonas, Bacillus, Escherichia, Enterococcus, and Klebsiella;
- (b) exposing said bacteria to biological, chemical or physical stress so that the bacteria release a stress release product into the medium;
- (c) removing said bacteria from said medium and said stress release product to form a separated product; and
- (d) filtering said separated product through a filter having a 10,000 dalton molecular weight cutoff to obtain said stress release product.

13. The method according to claim 1 wherein the bacteria is selected from the group consisting of *L. acidophilus, L. caseii, L. fermentum, L. plantarum, L. monocytogenes, S. aureus, S. typhimurium, P. acidolactici, B. coryneforme, E. coli, E. faecium, S. pyogenes*, and *K. pneumoniae*.

14. A method for activating and modulating the immune system of an animal comprising:
- (a) growing bacteria in a medium, wherein the bacteria is selected from the group consisting of *L. acidophilus, L. caseii, L. fermentum, L. plantarum, L. monocytogenes, S. aureus, S. typhimurium, P. acidolactici, B. coryneforme, E. coli, E faecium, S. pyogenes*, and *K. pneumoniae*;
- (b) exposing said bacteria to biological, chemical or physical stress such that the bacteria release a stress release product;
- (c) removing said bacteria from said medium and said stress release product to form a separated product;
- (d) filtering said separated product through a filter having a 10,000 dalton molecular weight cutoff to obtain said stress release product; and
- (e) administering an effective amount of said stress release product to said animal.

* * * * *